US006411087B1

(12) United States Patent
Fan et al.

(10) Patent No.: US 6,411,087 B1
(45) Date of Patent: Jun. 25, 2002

(54) NMR LOGGING TOOL WITH HI-TC TRAP FIELD MAGNET

(75) Inventors: Nongqiang Fan, Redmond, WA (US); Wei-Kan Chu, Pearland, TX (US)

(73) Assignee: University of Houston, Houston, TX (US)

( * ) Notice: Subject to any disclaimer, the term of this patent is extended or adjusted under 35 U.S.C. 154(b) by 0 days.

(21) Appl. No.: 09/567,731

(22) Filed: May 10, 2000

Related U.S. Application Data (60) Provisional application No. 60/134,441, filed on May 17, 1999.

(51) Int. Cl.[7] .................................................. G01V 3/00
(52) U.S. Cl. ........................................ 324/303; 324/300
(58) Field of Search ................................ 324/303, 300, 324/318, 322, 319; 335/306, 300, 216

(56) References Cited

U.S. PATENT DOCUMENTS

| | | | |
|---|---|---|---|
| 4,350,955 A | 9/1982 | Jackson et al. | 324/303 |
| 4,933,638 A | 6/1990 | Kenyon et al. | 324/303 |
| 5,280,243 A | 1/1994 | Miller | 324/303 |
| 5,488,342 A | 1/1996 | Hanley | 335/306 |
| 5,537,829 A | 7/1996 | Jones et al. | 62/51.1 |
| 6,025,769 A * | 2/2000 | Chu et al. | 335/216 |

OTHER PUBLICATIONS

M. Morita et al., Trapped Fields and Mechanical Properties of OMG Bulk Magnets; The 1998 International Workshop on Superconductivity, Jul. 12–15, 1998; Okinawa, Japan.

H. Fujimoto et al., A Superconducting Bulk Magnet for the Maglev Train: Preliminary Study; The 1998 International Workshop on Superconductivity; Jul. 12–15, 1998; Okinawa, Japan.

R. Weinstein, et al. *Very High Trapped Fields: Cracking, Creep, and Pinning Center*; pp. 625–628.

Yukikazu Iwasa, Electromaglev ("Active–Maglev")—Recent Results; The 1998 International Workshop on Superconductivity, Jul. 12–15, 1998, Okinawa, Japan.

\* cited by examiner

*Primary Examiner*—Edward Lefkowitz
*Assistant Examiner*—Brij B. Shrivastav
(74) *Attorney, Agent, or Firm*—Madan, Mossman & Sriram, P.C.

(57) ABSTRACT

Trapped field magnets (TFMS) on an NMR logging tool are used to produce a static magnetic field in a formation surrounding a borehole. The TFMs are made of material having a high $T_c$, so that the magnetic field can be sustained for the duration of the well logging by enclosing the TFMs within a cryostat containing liquid nitrogen as a coolant. By using the TFMs, the field strength within this region is much higher than is attainable with conventional magnets, giving an improved signal to noise (S/N) ratio for the NMR signals. The magnetic field strength within the TFMs is kept at a low enough value that instability problems associated with these materials do not arise. The field strength may be selected based upon knowledge of the resistivity and dielectric constant of the formation and the associated skin depth for electromagnetic signals. This makes it possible to use the TFMs in both wireline and measurement while drilling (MWD) environments. In one embodiment of the invention, the TFMs are magnetized outside the borehole environment using conventional high field strength electromagnets prior to emplacement within the cryostats. In another embodiment of the invention, vortex currents within the TFMs are induced in situ over a period of time, so that the power requirements for the inducing field are attainable in a borehole environment. A pulsed radio frequency (RF) magnetic field is produced using an RF antenna in the NMR tool that is orthogonal to the direction of the static magnetic field. The NMR pulse echo signals induced in the formation indicative of a parameter of interest in the formation is received by a receiver on the tool

19 Claims, 5 Drawing Sheets

NMR LOGGING TOOL WITH HI-TC TRAP FIELD MAGNET

CROSS-REFERENCES TO RELATED APPLICATIONS

This application claims priority from United States Provisional Patent Application 60/134,441 filed on May 17, 1999.

BACKGROUND OF THE INVENTION

1. Field of the Invention

This invention relates to nuclear magnetic resonance and more particularly to a nuclear magnetic resonance apparatus and method using high static magnetic fields trapped in high temperature superconducting materials.

2. Description of the Related Art

A variety of techniques have are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, tools designed to provide the desired information are used to log the wellbore. Much of the logging is done after the well bores have been drilled. More recently, wellbores have been logged while drilling of the wellbores, which is referred to as measurement-while-drilling ("MWD") or logging-while-drilling ("LWD").

When logging is done after the wellbores have been drilled, a sensor assembly is conveyed downhole on a wireline that includes electrically conducting cables for carrying electrical power downhole and for transmission of signals in an uphole and a downhole direction.

In MWD applications, a drilling assembly (also referred to as the "bottom hole assembly" or the "BHA") carrying a drill bit at its bottom end is conveyed into the wellbore or borehole. The drilling assembly is usually conveyed into the wellbore by a coiled-tubing or a drill pipe. In the case of the coiled-tubing, the drill bit is rotated by a drilling motor or "mud motor" which provides rotational force when a drilling fluid is pumped from the surface into the coiled-tubing. In the case of the drill pipe, it is rotated by a power source (usually an electric motor) at the surface, which rotates the drill pipe and thus the drill bit.

Bottom hole assemblies generally include several formation evaluation sensors for determining various parameters of the formation surrounding the BHA during the drilling of the wellbore. Such sensors are usually referred to as the MWD sensors. Such sensors traditionally have electromagnetic propagation sensors for measuring the resistivity, dielectric constant, water saturation of the formation, nuclear sensors for determining the porosity of the formation and acoustic sensors to determine the formation acoustic velocity and porosity. Other downhole sensors that have been used or proposed for use include sensors for determining the formation density and permeability. The bottom hole assemblies also include devices to determine the BHA inclination and azimuth, pressure sensors, temperature sensors, gamma ray devices, and devices that aid in orienting the drill bit in a particular direction and to change the drilling direction. Acoustic and resistivity devices have been proposed for determining bed boundaries around and in some cases in front of the drill bit. More recently, nuclear magnetic resonance (NMR) sensors have gained extreme interest as MWD sensors as such sensors can provide direct measurement for water saturation porosity and indirect measurements for permeability and other formation parameters of interest.

NMR tools generate a near uniform static magnetic field in a region of interest surrounding the wellbore. The NMR measurement is based on the fact that the nuclei of many elements possess angular momentum ("spin") and a magnetic moment. In the absence of an external field, the nuclear spin orientations are randomly distributed with an essentially uniform orientation in space, but when a magnetic field is applied, the nuclei tend to align themselves in one of two quantum states: either parallel or anti-parallel to the applied field. There is a net excess of spins aligned parallel to the field, so that on a macroscopic level, the material in the region of interest takes on a net magnetization aligned in the same direction as the applied magnetic field. The stronger the magnetic field, the greater the excess of parallel spins and the stronger the net magnetization. NMR sensors utilize permanent magnets to generate a static magnetic field in the formation surrounding the MWD tool.

For the purposes of this invention, the NMR measurements may be treated on a macroscopic scale rather than a quantum scale. The region surrounding the NMR tool can be uniformly divided into a grid of volume elements, commonly termed "voxels," that can be referenced using a suitable coordinate system. One such convenient coordinate system is a cylindrical polar coordinate system. Each voxel contains many hundreds of thousands of nuclei, but each voxel is small in comparison with the dimensions of the sensor. Within each voxel, the static magnetic field can be represented by a vector $B_0$ and the magnetization by a vector M, both with classical properties. In this way, the quantum nature of the NMR phenomenon may be conveniently set aside. Hereafter, the magnetization in the voxels is loosely referred to as "spin."

In equilibrium conditions, the quantities $B_0$ and M are related by the expression $$M = \frac{N_A \gamma^2 \hbar^2 I(I+1)}{3kT} B_0 \qquad (1)$$

where $N_A$ is Avogadro's number, $\gamma$ is the gyromagnetic ratio of the nucleus, h is Planck's constant, I is the nuclear spin, k is Boltzmann's constant, and T is the absolute temperature. Associated with the magnetic field strength $|B_0|$ is a characteristic frequency, called the Larmor frequency, given by $$\omega_0 = \gamma |B_0| \qquad (2)$$

The equilibrium condition can be disturbed by applying a pulse of an oscillating magnetic field, represented by $B_1$; this is called a radio frequency or RF pulse. Spins that have Larmor frequency at or near the frequency of the applied oscillating magnetic field experience a torque, as described by the Larmor equation $$\frac{dM}{dt} = M \times \gamma B_0 \qquad (3)$$

where x denotes the vector cross product. This expression describes a resonant condition: spins with a Larmor frequency that matches the applied field frequency are tipped away from the static field direction by an angle (in radians) given by the equation $$\theta = \gamma |B_1| t_p / 2 \quad (4)$$

where $t_p$ is the duration of the pulse.

Those spins "on resonance," i.e., having a Larmor frequency that exactly matches the applied oscillating field will precess around the static field at the Larmor frequency. At the same time, the spins return to the equilibrium direction, i.e., aligned with the static field, according to a characteristic decay time constant known as the "spin-lattice relaxation time" or "T1."

For hydrogen nuclei, $\gamma/2\pi = 42.58$ MHz/T, so that a static field of 0.0235 Tesla, would produce a precession frequency of 1 MHz. U.S. Pat. No. 4,933,638 discloses a wireline NMR logging tool that operates at a frequency of 1 MHz, which is typical of prior art tools. The decay constant T1 is controlled by the molecular environment and is typically ten to one thousand ms. in rocks.

At the end of a ninety degree tipping pulse, all the spins on resonance are pointed in a common direction perpendicular to the static field, and they all precess at the Larmor frequency. The precessing spins are detected by a voltage induced in a receiving coil. This may be the same coil as used to produce the $B_1$ field or another suitably oriented coil. According to the principle of reciprocity the component of nuclear magnetization that is precessing in a plane perpendicular to the field that would be produced by current flowing in the receiving coil induces a voltage in the receiver coil that can be amplified and measured. The voltage appearing on the receiver coil is the summation of all signals from the precessing spin system in the region of interest. The decay of the precessing pulses gives useful information about the fluid content in the formation surrounding the borehole. In particular, the dominant contribution to the signal arises from the precession of hydrogen nucleii and are thus a good indicator of the amount of water and hydrocarbons in the formation.

The magnets and the RF coils are positioned so that the static and the RF fields are perpendicular to each other at least over a portion of the formation surrounding the NMR tool where the static field has a substantially uniform strength. This region is the region of interest or region of examination. The NMR measurements corresponding to such region are needed to determine the formation parameters of interest. At the field strengths typically used in NMR tools, the region of examination can overlap a part of the wellbore, which can severely affect the formation measurements due to the fluid in the wellbore.

A problem with prior art techniques is that the signal to noise ratio of the precessing signals is small. As noted above, the net magnetization is a function of the excess of those spins that are aligned parallel to the applied magnetic field and those spins that are aligned anti-parallel to the applied magnetic field. This excess is primarily a function of the strength of the applied magnetic field.

It would be desirable to have an NMR logging tool in which much higher magnetic fields are used than in prior art: this would facilitate having the region of examination further away from the borehole while, at the same time, increasing the signal to noise ratio of the NMR signals. The present invention satisfies this need.

SUMMARY OF THE INVENTION

The present invention discloses a method and apparatus for determining a characteristic of an earth formation surrounding a borehole in which a pulsed nuclear magnetic resonance (NMR) tool is received. A static magnetic field is produced in the borehole using Trapped Field Magnets (TFMs). The term TFM refers to a superconducting material below its critical temperature $T_c$ having a circulating current therein, the current being able to flow indefinitely within the superconducting material, thereby sustaining a magnetic field. The TFMs are made of material having a high $T_c$, so that the magnetic field can be sustained for the duration of the well logging by enclosing the TFMs within a cryostat containing liquid nitrogen or liquid helium as a coolant, or using a cryocooler. The magnets are configured to provide a region of examination within the formation and at a distance form the borehole with the desired field strength. By using the TFMs, the field strength within this region is much higher than is attainable with conventional permanent magnets, giving a large signal to noise (SIN) ratio for the NMR signals. The magnetic field within the TFMs is kept at a low enough value that instability problems associated with these materials do not arise. This makes it possible to use the TFMs in an MWD environment. In one embodiment of the invention, the TFMs are magnetized outside the borehole environment using conventional high field strength electromagnets prior to emplacement within the cryostats. In another embodiment of the invention, vortex currents within the TFMs are induced in situ over a period of time, so that the power requirements for the inducing field are attainable in a borehole environment.

A radio frequency (RF) magnetic field is produced using a RF antenna in the NMR tool that is orthogonal to the direction of the static magnetic field. The RF magnetic field comprises a RF magnetic field modulated by a sequence of pulses. Such sequences of pulses are known in the art. An induced signal is received relating to a parameter of interest in the formations.

BRIEF DESCRIPTION OF THE DRAWINGS

The present invention may be better understood, and its numerous objects, features, and advantages made apparent to those skilled in the art by referencing the accompanying drawings.

The use of the same reference symbols in different drawings indicates similar or identical items.

DESCRIPTION OF THE PREFERRED EMBODIMENT

Figure 1A:
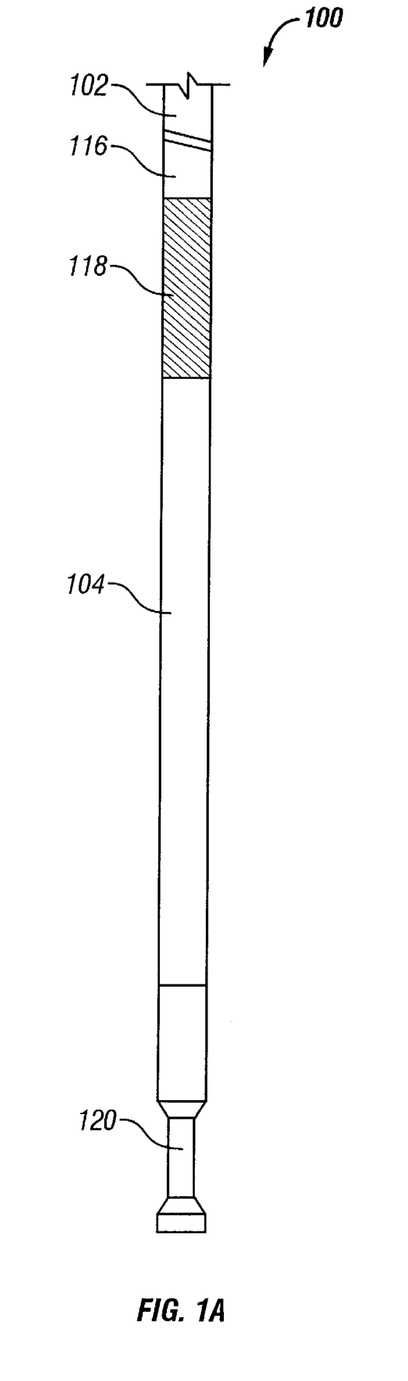
FIGS. 1A–1C are side elevational views partially in section of a drilling assembly including an NMR tool in accordance with the present invention.
Figure 1B:
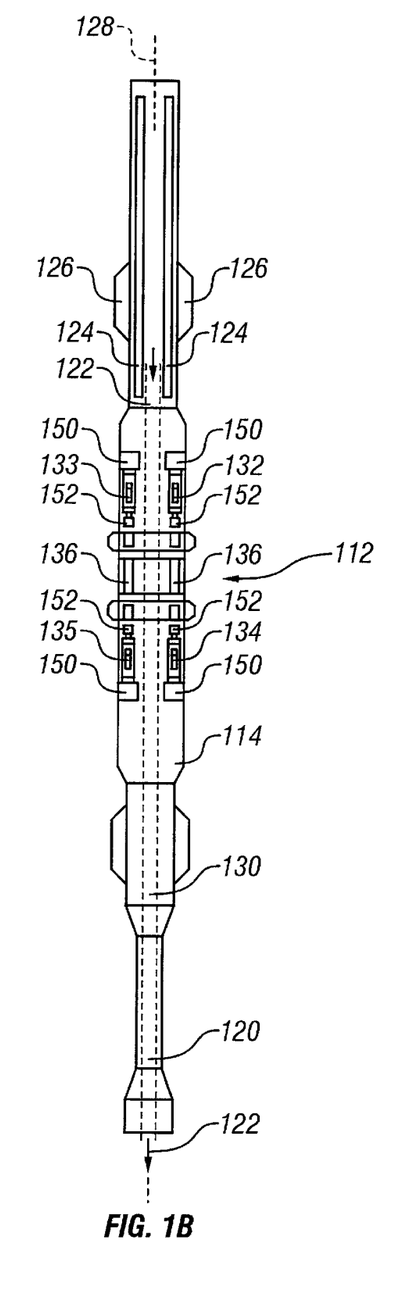
Figure 1C:
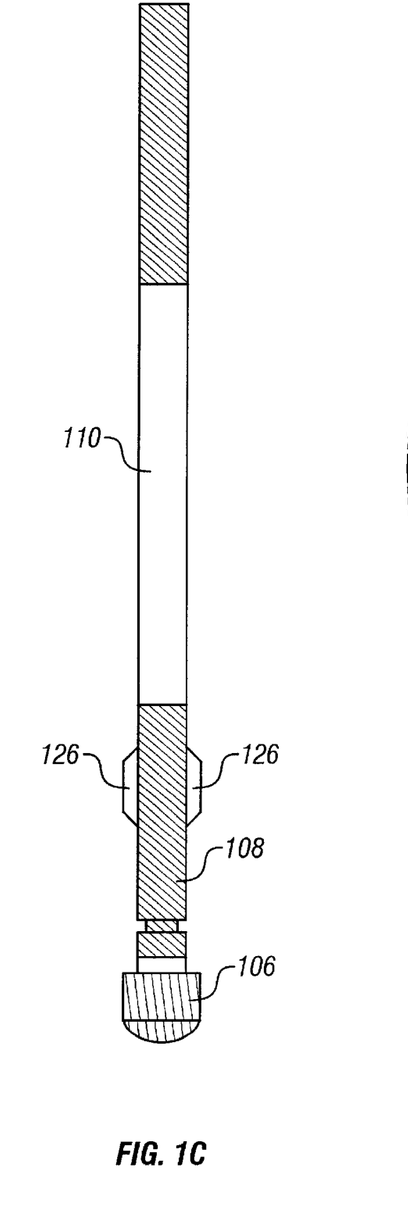

Referring to FIGS. 1A–1C, a drilling assembly 100 at the end of a drill string 102 or coiled tubing is illustrated according to the present invention. A measurement-while-drilling (MWD) tool 104, an associated pulsed nuclear magnetic resonance (NMR) tool 112 (contained within a housing 114) and electronic circuitry 124, and a pulsed power unit 118 are connected in tandem in the drilling assembly 100. Flex subs 120 are used for example in connecting the MWD tool 104 and the NMR tool 112 in the drilling assembly 100. The MWD tool 104 may also include a sonic sensor, a density measurement tool, and a porosity measurement tool. A communication sub 116 using, for example, two-way telemetry, is also provided as illustrated in the drilling assembly 100.

The drilling assembly 100 includes a drill bit 106, bearing assembly 108, and downhole mud motor 110. The drill string 102 includes, for example, sections of drill pipe connected end-to-end or a generally continuous coiled tubing. The borehole typically contains a drilling fluid 122 or "mud" which is forced through the drill string 102 and the bottom hole drilling assembly 100 through the drill bit 106. A channel 130 within the drill string 102 and drilling assembly 100 allows the drilling fluid 122 through the drill string 102 and drilling assembly 100. The drilling fluid acts to lubricate the drill bit 106 and to carry borehole cutting or chips away from the drill bit 106.

The communication sub 116, power unit 118, MWD tool 104, and NMR tool 112 are all connected in tandem with the drill string 102. Such subs and tools form a bottom hole drilling assembly 100 between the drill string 102 and the drill bit 106. Stabilizers 126 are used to stabilize and center the drilling assembly 100 and tools within the borehole. The housing 114, for example, a drilling collar, is made of a nonmagnetic alloy. The drilling assembly 100 makes various measurements including pulsed nuclear magnetic resonance measurements while the borehole is being drilled. As seen in FIG. 1B, the NMR tool is rotationally symmetric about a longitudinal axis 128 of the drilling assembly 100.

The pulsed NMR tool 112 includes at least two spaced-apart cryostats 132 and 134 housed in the drilling assembly 100 and within the NMR tool 112. The cryostats contain magnets (described below) for producing a static magnetic field having a region of substantially uniform magnetic intensity in the vicinity of the borehole. The at least two spaced-apart cryostats 132 and 134 are tubular in shape and arranged coaxially within the NMR tool 112 and to surround the channel 130. The cryostats 132 and 134 contain liquid nitrogen or helium as a coolant and tubular trapped field magnets (TFMs) 133 and 135 respectively. Details about the TFMs are discussed below with reference to FIGS. 4–6B.

A radio frequency (RF) transmitting antenna or coil 136 also surrounds the channel 130 and is located, for example, between the two spaced-apart magnets 133 and 135. The RF coil 136 is connected to a suitable RF pulse transmitter such as the pulsed power unit 118 for providing power at selected frequencies and electronic driving circuitry 124 which drives the RF transmitting antenna or RF coil 136. The RF coil 136 is pulsed and creates a high frequency RF field orthogonal to the static magnetic field. The TFMs are made of superconducting material having a high critical temperature $T_c$.

Figure 2:
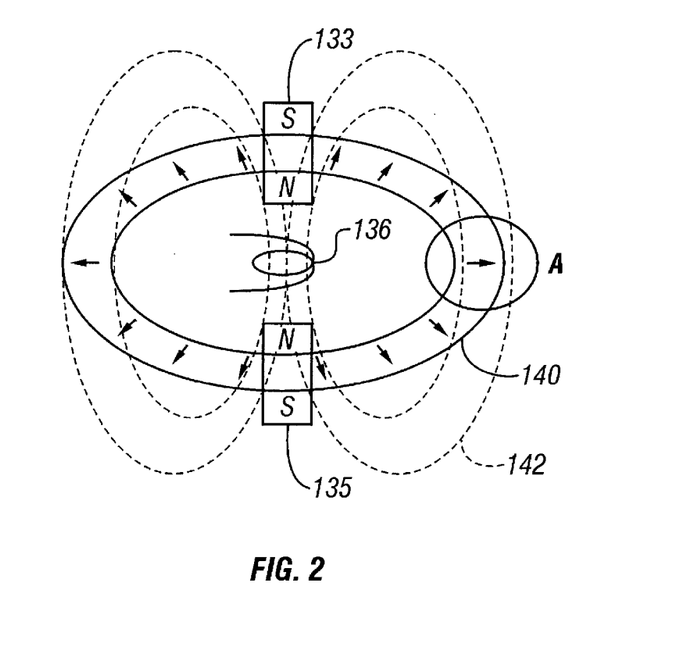
FIG. 2 illustrates the production of a toroidal region of homogeneous radial magnetic field perpendicular to a pair of axially aligned magnets having like adjacent poles and the application of a pulsed RF field to the magnetization.

The at least two TFMs 133 and 135 are positioned in opposing directions, as shown in FIG. 2. As shown in FIG. 2, like magnetic poles, for example, the north magnetic poles of the two magnets 133 and 135 face one another. Due to the fact that like poles of the magnet oppose each other, the magnetic field strength has a singularity midway between the magnets. In the plane midway between the magnets, the resultant field is substantially radial in direction and reaches a maximum value at some axial distance away from the magnets and then decreases at increasing distances. In the vicinity of the maximum is a toroidal region of substantially homogeneous radial magnetic field 140 (see FIG. 2) perpendicular to the pair of axially aligned magnets 133 and 135. The field in this toroidal region is radially symmetric.

Still referring to FIG. 2, the pulsed RF coil 136 creates the pulsed RF field 142 illustrated by dashed lines. The distance of the toroid from the borehole is a function of the magnetization of the RFMs, their size and their separation. Calculations of the magnetic field produced by the RFMs may be determined by suitable modeling methods, such as a Finite Element analysis and would be known to those versed in the art. Examples of such modeling calculations are given in U.S. Pat. No. 5,488,342 issued to Hanley. Rock pores (not shown) in the earth formations are filled with fluid, typically water or hydrocarbon. The hydrogen nuclei in the fluid are aligned in the region of homogeneous magnetic field 140, generated by the magnets 133 and 135 as discussed above. The hydrogen nuclei are then "flipped" away from the homogeneous magnetic field 140 by the pulsed RF field 142 produced by RF coil 136. At the termination of the pulsed RF field from RF coil 136, the hydrogen nuclei revolve or precess at high frequency around the substantially homogeneous magnetic field 140 inducing an NMR signal in the RF coil 136 until the hydrogen nuclei relax to the original direction along the homogeneous magnetic field 140. The induced NMR signals are sent to the surface for processing or can be processed by a downhole processor (not shown).

Figure 3:
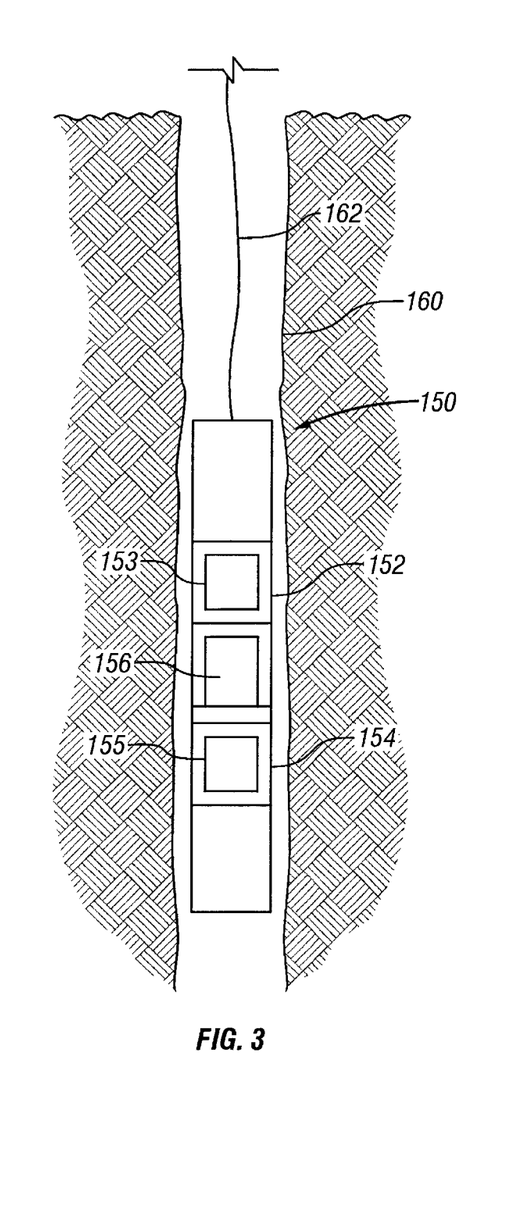
FIG. 3 shows an embodiment of the present invention suitable for use on a wireline.

FIG. 3 shows an embodiment of the present invention suitable for use on a wireline. Shown is a logging tool 150 conveyed on a wireline 162 within a borehole 160. The logging tool includes two cryostats 152, and 154 and the RFMs 153 and 155 contained therein. The RF coil section 136 is located between the two cryostats. For simplifying the illustration, other sensors on the logging tool 150, the electronics for activating the RF transmitter and signal processing equipment are not shown. The tool operates in substantially the same manner as the MWD tool described above with reference to FIGS. 1 and 2.

Other configurations of permanent magnets have been used in NMR applications. For example, U.S. Pat. No. 5,280,243 to Miller, the contents of which are fully incorporated here by reference, discloses a long cylindrical magnet in which the magnetic axis is perpendicular to the longitudinal axis of the magnet. TFMs may be used with this and any other suitable magnet configuration.

There are a number of ways in which the trapped field may be produced and maintained in the TFM. In one embodiment of the invention, an electromagnet at the surface is used to produce the trapped field in the TFM while the TFM is cooled down to the necessary temperature. Subsequently, the TFM may be placed in the cryostat in the downhole tool and maintained at the necessary operating temperature. An alternative is to provide pulses of electrical current to the TFM when it is below the critical temperature: the electrical pulses produce vortex currents in the TFM. In addition, pulses of electrical energy may be passed through a coil (not shown) to produce vortex currents while the tool is downhole. This may be done to either maintain the trapped field at a desired level, or to alter the strength of the trapped filed (increasing or decreasing the field) in accordance with requirements discussed below with reference to FIG. 7.

U.S. Pat. No. 5,023,551 issued to Kleinberg discloses an NMR pulse sequence for use in the borehole environment which combines a modified fast inversion recovery (FIR) pulse sequence with a series of more than ten, and typically hundreds, of CPMG pulses according to $$[W_i-180_x-t_i-90_x-(t_{ep}-180_y-t_{cp}-\text{echo})_j]_i \quad (5)$$

where j=1,2, . . . , J, and J is the number of echoes collected in a single CPMG sequence, i=1,2, . . . , I and I is the number of waiting times used in the pulse sequence, $W_i$ are the recovery times before the inversion pulse, $t_i$ are the wait times before a CPMG sequence, and $t_{cp}$ is the Carr-Purcell spacing.

The phase of the RF pulses 90 (the tipping pulse) and 180 (the refocusing pulse) is denoted by the subscripts X and Y, Y being phase shifted by π/2 radians with respect to X. The subscripts also conventionally relate to the axis about which rotation of the magnetization occurs during the RF pulse in a local Cartesian co-ordinate system centered on the nucleus in which the static magnetic field is aligned in the Z direction and the RF field in the X direction. This sequence can be used to measure both T1 and T2, but is very time consuming, limiting logging speed. If $t_{CP}$ is set to zero and the inverting pulse is omitted then the sequence defaults to standard CPMG for measuring T2 only.

A number of other prior art inventions, such as those disclosed in U.S. Pat. No. 5,363,041 issued to Sezginer, U.S. Pat. No. 5,381,092 issued to Freedman, and International Application WO 97/34167 of Prammer use variations of the CPMG pulse sequence. Any of these pulse sequences may be used with the present invention to obtain information about the earth formations.

Figure 4:
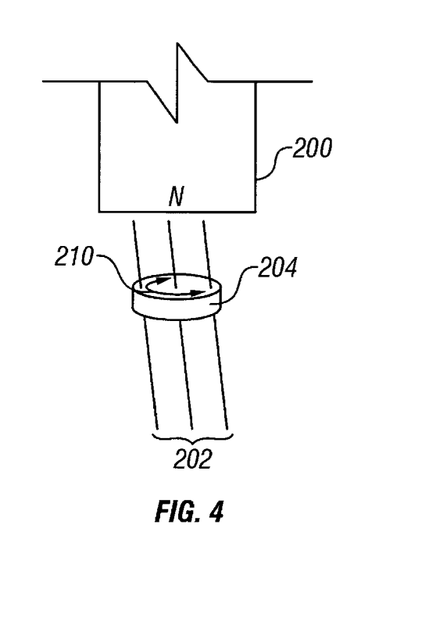
FIG. 4 shows a method of inducing a trapped field in a superconducting material.

In the embodiments of the invention discussed above, the RFMs are magnetized outside the wellbore by an intense magnetic field, such as that produced by an a electromagnet. FIG. 4 shows a disc 204 made of a superconducting material in the proximity of the North pole of a magnet 200 that may be an electromagnet. The magnetic flux lines of the magnet 200 are indicated by the arrows 202. When the superconducting material is below its $T_c$, a current is induced in the disc, the direction of the current being indicated by the arrow 210. When the disc 204 is removed from the vicinity of the magnet 200 and maintained below its $T_c$, the current will continue to flow in the disc 204 indefinitely. The magnetic field associated with this circulating current will be in a direction opposite to the direction of the field 202 that induced the circulating current. The disc 200 is now a TFM and when maintained in a cryostat containing liquid nitrogen, may be used in the embodiments of the invention described above. This assumes that the $T_c$ for the material is above the boiling point of liquid nitrogen.

Figure 5A:
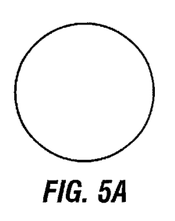
FIGS. 5A–5D shows various configurations of the component of a trapped field magnet.
Figure 5B:
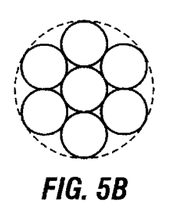
Figure 5C:
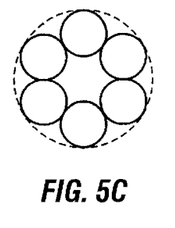
Figure 5D:
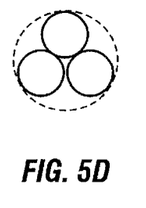

Iwasa et al. disclose various configurations that may be used for a TFM. These are shown in FIGS. 5A–5D. The direction of the circulating current for each of the configurations is also shown. The arrangement in FIG. 5A is able to maintain the largest magnetic field and is used in the present invention in wireline applications. Next in the magnitude of the magnetic flux is the arrangement in FIG. 5B. which also has the advantage of being easier to fabricate and is used in an alternate embodiment of the present invention for wireline applications. The arrangement shown in FIG. 5C is suitable for use in an MWD environment and the preferred embodiment of the present invention for MWD applications uses six discs arranged outside the inner channel 130 of the tool (See FIG. 1).

There are two methods used in prior art for producing a TFM. In the first method, a TFM is produced by applying a large external magnetic field to a superconducting material below its critical temperature, and reducing the applied field to zero. In the second method, an external magnetic field equal to the final desired field of the TFM is applied to a superconducting material above its critical temperature and then lowering the temperature of the material to below its critical temperature. Subsequently, as long as the material is maintained below the critical temperature, the currents within the material will keep circulating and thereby maintain the trapped field. Weinstein et al. disclose the use of sintered materials to produce disc shaped TFMs that can sustain magnetic fields as large as 10 Tesla. Methods for dealing with number of problems associated with a TFM are disclosed in Weinstein et al.

During the process of reducing the external field, a voltage is induced in the superconducting disc given by $$V_{induced} = -A \frac{dB_A}{dt} \quad (6)$$

where $V_{induced}$ is the induced voltage, A is the area of the superconducting disc and $B_A$ is the applied external flux. When the induced voltage exceeds 0.1 μV, flux jump may occur. However, the problem of flux jump is not serious when at the maximum applied fields of less than 2 Tesla in the present invention.

A second problem addressed by Weinstein et al. is that of creep, i.e., slow mechanical deformation of the TFM, accompanied by a change in the magnetic field. Creep is fairly accurately represented by the relation $$B_1(t_2) = B_1(t_1)\left[1 - \beta\log\left(\frac{t_2}{t_1}\right)\right] \quad (7)$$

between the fields at times $t_1$, and $t_2$. By using a process of post activation cooling wherein the temperature T is reduced by an amount ΔT after the applied field has reached zero, Weinstein shows that the creep is reduced almost to zero for a post activation cooling temperature ΔT of 6° K.

Another problem that arises with TFMs is the Lorentz force, which produces an outward pressure of $J \times B_r$ in an object carrying a current J with a field strength of $B_r$. Yen et al. developed a generalized theory of cracking to apply to the dynamic conditions that prevail during activation of the magnetic field. One of the requirements arising from Yen et al is the condition noted above, i.e., that the applied field should be approximately equal to the desired trapped field.

There are devices for use of a cryostat in borehole applications. Some of these are discussed in U.S. Pat. No. 4,248,298; 4,312,192; 4,313,317; 4,315,417. Use of any of these, or other devices, in the present invention is relatively easy due to the small size, of the order of a few centimeters, of the TFMs: this is in contrast to the larger sizes of the permanent magnets (of the order of tens of centimeters) for prior art NMR tools and the other logging tools for which cryostats have been used in logging applications. In another embodiment of the invention (not shown) cryocoolers are used instead of cryostats, and the trapped magnetic field is produced downhole by using electromagnets. Due to the fact that it takes relatively small amount of energy to produce the trapped field once the superconductor has been cooled to below the critical temperatures, the energy requirements for producing the trapped field may be readily obtained either in wireline applications or by using a downhole turbine driven by the drilling mud in an MWD environment.

In an alternative embodiment, the at least two TFMs 133 and 135 are magnetized in the axial direction and are positioned in the same direction. For example, the north magnetic pole of one magnet 135 faces the south magnetic pole of the other magnet 133 for producing a static magnetic field having a region of substantially uniform magnetic intensity in a longitudinal direction and parallel to the pair of axially aligned magnets 133 and 135. In such a magnetic assembly, the RF coil 136 is pulsed and creates a high frequency RF field in the radial direction, orthogonal to the static magnetic field, for producing a region or volume of interest for NMR signal sensitivity.

The apparatus of the present invention is not limited to the illustrated magnet assembly and arrangement. For example, in another embodiment, the at least one pair of magnets 133 and 135 can include a plurality of stacked tubular permanent magnets aligned with the longitudinal axis 128 of the NMR tool 112. The stacked tubular magnets can be arranged in pairs on opposite sides of a symmetry plane (see the magnets 133 and 135 shown in FIG. 2) with magnetic poles of each pair of magnets in opposition. A cylinder of ferrite (a ferrite yoke) may be placed between the tubular magnets for concentrating the magnetic flux. The static magnetic field produced by the magnet/yoke arrangement is a toroidal radial magnetic field centered on the longitudinal axis 128 of the NMR tool 112. However, the static magnetic field can also be produced in the longitudinal direction as previously describe, wherein the at least two spaced-apart magnets have opposing magnetic poles facing each which creates a static magnetic field in the longitudinal direction.

The apparatus of the present invention is also not limited to the illustrated sensor assembly and RF coil arrangement. Any number of appropriate antenna or coil arrangements that provide a RF field orthogonal to the static magnetic field direction for creating the region of interest for NMR signal sensitivity can be used according to the present invention. For example, the NMR tool can employ separate transmitter and receiver coils.

Figure 6A:
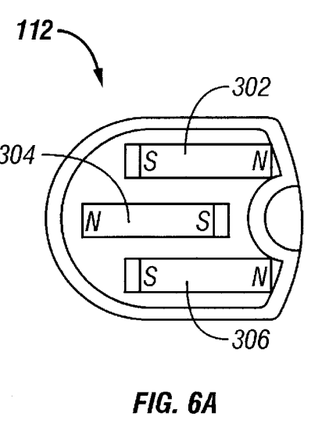
FIGS. 6A and 6B are sectional view of another embodiment of an NMR tool illustrating the use of three TMF elements in a wireline logging accordance with the present invention.
Figure 6B:
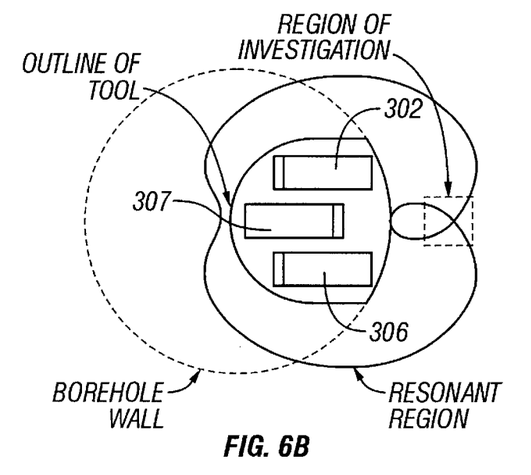

The NMR tool 112 shown in FIGS. 6A and 6B is particularly suitable for wireline applications. The magnets 302, 304 and 306 produce a static magnetic field 308 having a saddle point at the center of a homogeneous field region as shown in FIG. 8B. With this configuration, the magnet array appears at a distance like a magnetic N pole. However, the reversed pole positioning of magnet 304 substantially alters the magnetic field at close and intermediate distances from the NMR tool 112. The magnets 302, 304 and 306 produce a field anomaly within a defined region or volume of examination 316 directly in front of the NMR tool 112 face.

While the present invention may be operated at magnetic fields strengths of as large as 2 Tesla, giving a Larmor frequency of approximately 100 MHz, it may not always be desirable to operate at these high field strengths even though the induced NMR signal would be much larger than at lower frequencies. The reason for this is the frequency dependent value of the conductivity and the dielectric constant of the formation rocks.

Figure 7:
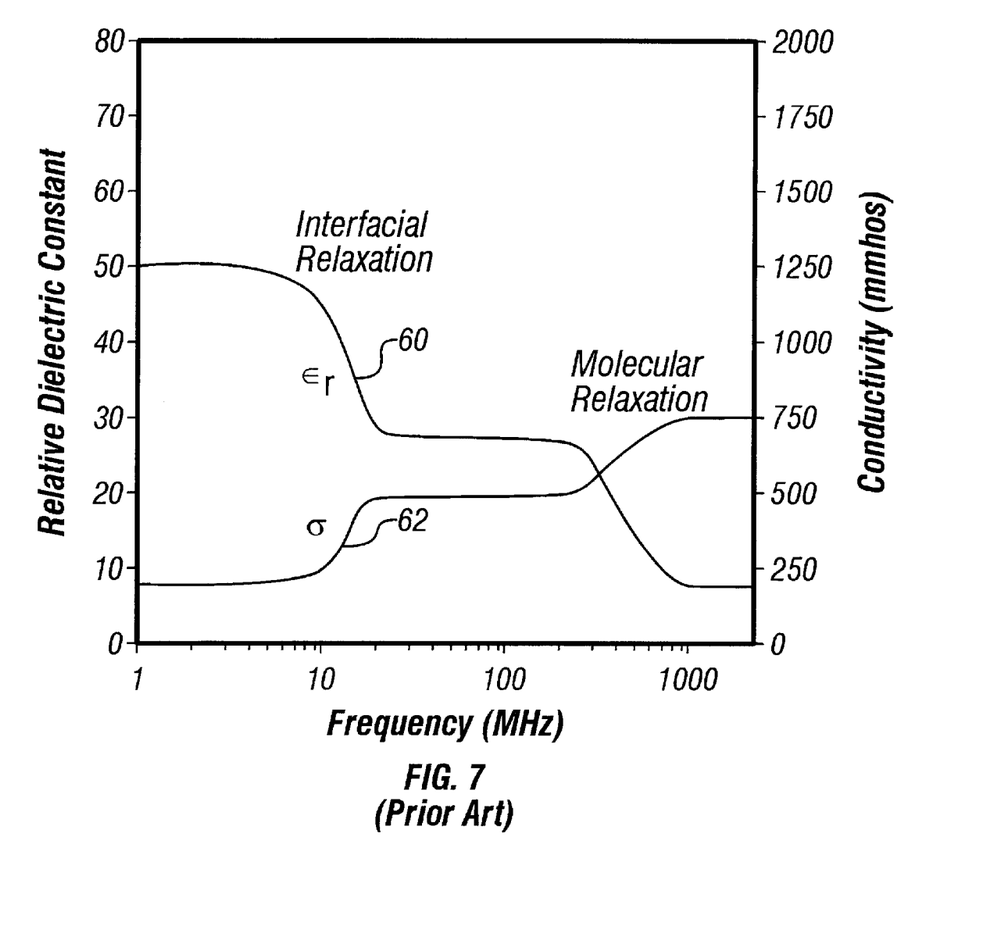
FIG. 7 shows an example of dispersion curves of water saturated sandstone.

FIG. 7 reproduced from U.S. Pat. No. 5,811,973 issued to Meyer et al. shows a theoretical dispersion curve for sandstones. The dispersion curves are associated with motion of water molecules within the formation and show two distinct relaxation frequencies at approximately 10 MHz and 400 MHz. As discussed in Meyer et al., the propagation of a plane electromagnetic wave in a medium is given by an equation of the form $$V = Ce^{ikx} \quad (8)$$

where C is a constant, x is the distance traveled and k is a wavenumber given by $$k = [(\omega^2 \mu_0 \mu_r \epsilon_0 \epsilon_r) + i\omega\mu_0\mu_r\sigma]^{1/2} \quad (9)$$

where
  c=the speed of light=2.999×10$^8$ meters/sec,
  $\mu_0$=the magnetic permeability of free space=4×10$^{-7}$,
  $\mu_r$=the relative magnetic permeability, approximately equal to 1.0 for most earth materials,
  $\epsilon_0$=the electric permittivity of free space=8.854×10−12,
  $\epsilon_r$=the relative dielectric constant of the material,
  $\omega$=angular frequency of the applied field, and
  $\sigma$=conductivity of the material.
This may be rewritten as $$k = k_0\sqrt{\epsilon_c \mu_r} \quad (10)$$

Where
  $k_0$ is the wavenumber in free space,
  $\mu_r$=1.0, and
  $\epsilon_c$ is a complex dielectric constant given by $$\varepsilon_c = \varepsilon_r + i\frac{\sigma}{\omega\varepsilon_0} \quad (11)$$

The imaginary part of the wavenumber k gives the attenuation of the wave in the medium. The value of this, after proper substitution above, turns out to be $$\alpha = \frac{\sigma}{2c\varepsilon_0\varepsilon_r^{1/2}} \quad (12)$$

Substituting a value of $\sigma$ equal to 200 mmhos and $\epsilon_r$=50 from FIG. 7 gives an attenuation of 5.5 nepers/meter at 1 MHz for prior art tools. Substantially the same value of the attenuation is obtained at a frequency of 10 MHz for the present invention. A Larmor frequency of 10 MHz corresponds to a field of 0.235 Tesla. At higher field strengths, due to the increased conductivity and the reduced relative dielectric constant, the attenuation would be greater.

In the present invention, when it is operated above the interfacial relaxation frequency, there is a tradeoff between the higher NMR signal obtainable with the higher magnetic field and the increased decay that results above the interfacial relaxation frequency. Accordingly, in a preferred embodiment of the invention, a propagation resistivity tool is used to obtain information about the formation resistivity and dielectric constant. Based upon this knowledge, the separation between the magnets and/or the maximum field strength of the TFMs is changed to provide an increased NMR signal from the region of examination at the receiver coil position. The alteration in field strength of the TFMs may be done either at the surface or by pulsing currents through a coil (not shown) so as to induce vortex currents in the TFM.

While the embodiment of the invention has been discussed with reference to an MWD assembly conveyed on a drillstring, those versed in the art would recognize that the invention could be practiced in other environments as well, such as on an MWD assembly carried on coiled tubing, on a bottom hole assembly for use in measurement while tripping, or on a wireline. These are intended to be within the scope of the appended claims.

While preferred embodiments have been shown and described, various modifications and substitutions may be made thereto without departing from the spirit and scope of the invention. Accordingly it is to be understood that the present invention has been described by way of illustrations and not limitations.

What is claimed is:

1. An apparatus for obtaining information about a parameter of interest of a formation surrounding a borehole, said apparatus comprising:

(a) a trapped field magnet arrangement for generating a static magnetic field in a region of examination of the formation;

(b) a temperature control device for maintaining the trapped field magnet arrangement below a critical temperature of material comprising the trapped field magnet arrangement;

(c) a radio frequency (RF) transmitter for generating a pulsed RF magnetic field having a frequency and a direction substantially orthogonal to a direction of the static magnetic field in the region of examination, said RF transmitter exciting nuclei in the region of examination; and (d) a RF receiver for receiving nuclear magnetic resonance signals from the excited nuclei and providing an output signal indicative of the parameter of interest.

2. The apparatus of claim 1 wherein the trapped field magnet arrangement further comprises at least two trapped field magnets (TFMs) having their magnetic axes parallel to a longitudinal axis of the borehole.

3. The apparatus of claim 1 wherein the trapped field magnet arrangement further comprises a cylindrical trapped field magnet (TFM) wherein a magnetic axis of the TFM is orthogonal to a longitudinal axis of the cylinder and a longitudinal axis of the borehole.

4. The apparatus of claim 1 further comprising a coil in the proximity of the trapped field magnet arrangement, said coil carrying pulses of electrical current for inducing vortex currents in the trapped field magnet arrangement, thereby altering a strength of said static magnetic field.

5. The apparatus of claim 1 wherein the temperature control device is selected from the group consisting of (i) a cryostat, and (ii) a cryocooler.

6. The apparatus of claim 2 wherein each of the at least two trapped field magnets further is selected from the group consisting of (i) a single disc-shaped magnet, (ii) six disc-shaped magnets disposed circumferentially around a central disc-shaped magnet, and (iii) six disc shaped magnets disposed circumferentially about an inner channel of The apparatus.

7. The apparatus of claim 1 wherein said pulsed RF magnetic field includes a CPMG sequence of pulses.

8. The apparatus of claim 1 wherein the trapped field magnet arrangement further comprises a sintered material.

9. The apparatus of claim 1 wherein the frequency of the pulsed RF magnetic field is selected based in part on a known value of resistivity and a known value of dielectric constant of the formation.

10. A method of obtaining information about a parameter of interest of a formation surrounding a borehole, said method comprising:

(a) using a trapped field magnet arrangement on a logging tool disposed in the borehole for generating a static magnetic field in a region of examination of the formation;

(b) using a radio frequency (RF) transmitter for generating a pulsed RF magnetic field having a direction substantially orthogonal to a direction of the static magnetic field in the region of examination, said RF transmitter exciting nuclei in the region of examination; and (c) receiving with a RF receiver on the logging apparatus nuclear magnetic resonance signals from the excited nuclei and providing an output signal indicative of the parameter of interest.

11. The method of claim 10 further comprising using one of (i) a cryostat, and, (ii) a cryocooler, on the logging tool for maintaining the trapped field magnet arrangement below a critical temperature.

12. The method of claim 10 further comprising using an electromagnet to achieve a desired field strength in the trapped field magnet arrangement.

13. The method of claim 10 further comprising determining a desired frequency of the pulsed RF magnetic field and a desired field strength in the trapped field magnet arrangement from obtained values of the resistivity and dielectric constant of the formation surrounding the borehole.

14. The method of claim 13 further comprising making measurements with a resistivity logging tool in the borehole and obtaining therefrom said values of resistivity and dielectric constant of the formation.

15. The method of claim 10 wherein the pulsed RF field includes a CPMG sequence.

16. The method of claim 10 further comprising using an electromagnet for producing a field strength in the trapped field magnet arrangement close to a desired field strength.

17. The method of claim 13 further comprising using an electromagnet for producing a field strength in the trapped field magnet arrangement close to the desired field strength.

18. The method of claim 16 further comprising using a coil on the logging tool for inducing vortex currents in the trapped field magnet arrangement and maintaining the field strength therein close to the desired field strength.

19. The method of claim 17 further comprising using a coil on the logging tool for inducing vortex currents in the trapped field magnet arrangement and maintaining the field strength therein close to the desired field strength.

* * * * *